US00PP10378P

United States Patent [19]

Tanaka et al.

[11] Patent Number: Plant 10,378

[45] Date of Patent: May 5, 1998

[54] FUCHSIA PLANT, SANIHANF

[75] Inventors: Toshi Tanaka, Ahiya; Hidefumi Funakoshi, Takarazuka; Kenkichi Nose, Ashiya; Ushio Sakazaki, Hikone, all of Japan

[73] Assignees: Suntory Limited, Osaka; Nishinomiya City, Hyogo, both of Japan

[21] Appl. No.: 788,461

[22] Filed: Jan. 28, 1997

[51] Int. Cl.[6] ..... A01H 5/00

[52] U.S. Cl. ..... Plt./84

[58] Field of Search ..... Plt./84

*Primary Examiner*—James R. Feyrer

*Attorney, Agent, or Firm*—Burns, Doane, Swecker & Mathis, L.L.P.

[57] ABSTRACT

Disclosed herein is a fuchsia plant, having a mutant growth habit plant with low plant height and being strongly bushy. The fuchsia plant has great profusion blooms, the whole bush remaining in bloom for a considerable period of time, and having a very long flowering duration. The flowers are single and not having variegated pattern on petals, the petals having a deep violet to moderate purple color, and having vivid red sepals without variegated pattern and vivid red calyx tube without variegated pattern. The plant has a high resistance to heat, cold and disease, and medium resistance to pests, and it is able to grow in an outdoor garden during the term of intense summer heat.

2 Drawing Sheets

BACKGROUNID OF THE VARIETY

The present invention relates to a new and distinct variety of fuchsia plant obtained from the crossing of one fuchsia plant "FR14" (♂) native to Brazil and the other fuchsia plant "Fuchsia hybrida 2"(♀).

The fuchsia plant is a very popular plant in the United States and Europe and is used for potting in the spring season to summer season. But fuchsia plants have a low resistance to heat and it is necessary to grow them in air-conditioned rooms during periods of intense heat.

Especially in Japanese summer, the heat is intense and it is necessary that the fuchsia plants grow in air-conditioned room, so the fuchsia plants have not become popular. Accordingly, this invention was aimed at obtaining a new variety having a strong resistance to heat and mutant growth habit.

The new variety of fuchsia plant according to this invention originated from crossing one fuchsia plant called "FR14" (♂) native to Brazil and the other fuchsia plant "Fuchsia hybrida 2"(♀).

First of all, one wild type of fuchsia plant called "FR14" was selected from 190 fuchsia plant varieties native to Brazil and introduced to Japan in Feburary, 1991, as seeds which were germinated. And then 150 seedlings were obtained from crossing the wild type of fuchsia plant called "FR14" native to Brazil as pollen parent and the other fuchsia plant "Fuchsia hybrida 2" as female parent in the spring, 1993. From this crossing, 9 seedlings were selected in view of heat resistance and growth habit. These 9 seedlings were grown and carried out a trial by flower potting in open-air field from the spring of 1994. The summer of 1994 had abnormal weather which was more intense than usual. One plant which could be grown in open-air conditions and had excellent results in apical meristem culture testing was selected in Autumn, 1994.

The botanical characteristics of the finally-selected one plant were examined, using similar variety "Fuchsia hybrida 2" and "Fuchsia hybrida 1" for comparison, from the spring of 1994. As a result, it was concluded that this fuchsia is distinguishable from any other variety, whose existence is known to us, sufficiently uniform and stable in its characteristics, then this new variety of fuchsia plant was named "Sanihanf".

In the following description, the color-coding is in accordance with The Horicultural Color Chart of The Royal Horticultural Society, London, England (R.H.S. Colour Chart), and the Inter-Society color Council-Nation Bureau of the Standard Color Name (I.S.C.C.-N.B.S. Color Name). A color chart based on The Japan Color Standard for Horticultural Plants (J.H.S. Color Chart) is also added for reference.

The pollen parent used in the crossing of "Sanihanf" was a wild type of fuchsia plant called "FR14" native to Brazil, the seeds introduced to Japan in February, 1991. The fuchsia plant "FR14" having a nutant growth habit, bright red colored sepals, single flowers, deep violet colored petal, and a high resistance to heat.

The female parent use in the crossing of "Sanihanf" was "Fuchsia hybrida 2". "Fuchsia hybrida 2" was a garden variety and was brought in a shop in the spring of 1992 in Hyogo-ken, Japan.

The wild type of fuchsia plants "FR14" and the garden variety "Fuchsia hybrida 2" are presently maintained at the Plant Biotechnology Laboratory of SUNTORY Ltd., residing at 863-1, Aza-Iketani, Oomori-cho, Youkaichi-shi, Shiga-ken, Japan and the Plant Research Center of NISHINOMIYA-SHI, residing at 1-1, Kitayama-cho, Nishinomiya-shi, Hyogo-ken, Japan.

"Fuchsia hybrida 2" which is the female parent of "Sanihanf" used for examination as a comparison is as follows.

Plant:

*Growth habit.*—Spreading.

*Plant height.*—Medium.

*Grade of bushiness.*—Few branches.

Stem:

*Thickness.*—1.7 mm.

*Color.*—Purplish red.

*Pubescence.*—Few.

*Branching.*—Medium.

*Length of internode.*—Short.

Leaf:
*Phyllotaxis.*—Opposite.
*Shape.*—Elliptic.
*Tip form of leaf.*—Acute.
*Base of form leaf.*—Orbicular.
*Shape of margin.*—Dentate serrate.
*Length.*—38.6 mm.
*Width.*—24.4 mm.
*Thickness.*—0.3 mm.
*Color of upper surface of new leaf.*—Moderate olive green. (R.H.S. 146A, JHS 3508).
*Color of upper surface of mature leaf.*—Dark olive green. (R.H.S. 132A, JHS 3708).
*Color of under surface of mature leaf.*—Strong yellow green. (R.H.S. 143A, JHS 3711).
*Variegation on upper surface.*—Absent.
*Color of leaf vein.*—Pale green.
*Luster.*—Weak.
*Pubescence of upper surface.*—Few.
*Pubescence of under surface.*—Few.
*Length of petiole.*—15.4 mm.
*Width of petiole.*—1.4 mm.
*Color of petiole.*—Moderate red (R.H.S. 184B, JHS 0115).
*Pubescence of petiole.*—Few.

Flower:
*Inflorescence types.*—Leaf axil—single.
*Facing direction.*—Downward to horizontal.
*Type.*—Double.
*Diameter.*—39.9 mm.
*Length.*—29.8 mm.
*Diameter of corolla.*—Medium.
*Shape of petal.*—Obovate.
*Length of petal.*—13.7 mm.
*Width of petal.*—13.5 mm.
*Thickness of petal.*—0.3 mm.
*Number of petals.*—Numerous; over 8.
*Color of petal at the beginning of blooming time.*—Deep purple (R.H.S. 86A, JHS 8307).
*Color of petal at blooming time.*—Deep purple. (R.H.S. 86A, JHS 8307).
*Variegated pattern of petal.*—Present; primary pattern is splashed pattern, secondary pattern is vein pattern.
*Color of variegated pattern of petal.*—Color of primary pattern is purple, color of secondary pattern is red.
*Shape of sepal.*—Ovate.
*Tip form of sepal.*—Acuminate.
*Calyx rolling.*—None (full down).
*Introsion of sepal.*—None.
*Curvature of sepal.*—Incurve.
*Length of sepal.*—18.3 mm.
*Width of sepal.*—11.2 mm.
*Thickness of sepal.*—0.5 mm.
*Number of sepals.*—Medium; 4.
*Color of sepal.*—Strong red.
*Variegated pattern on sepal.*—Absent.
*Shape of calyx tube.*—Long-tubular.
*Thickness of calyx tube.*—4.8 mm.
*Length of calyx tube.*—12.0 mm.
*Color of calyx tube.*—Strong purplish red. (R.H.S. 57D, JHS 9706).
*Variegated pattern on calyx tube.*—Absent.
*Length of pistil.*—Medium.
*Color of pistil.*—Vivid red. (R.H.S. 52A, JHS 0106).
*Color of stigma.*—Deep purplish pink. (R.H.S. 55A, JHS 9705).
*Length of stamen.*—Medium.
*Color of stamen.*—Vivid red. (R.H.S. 57A, JHS 0107).
*Number of stamens.*—Medium; 8.
*Thickness of peduncle.*—Medium..
*Color of peduncle.*—Moderate red. (R.H.S. 181B, JHS 0416).
*Shape of ovary.*—Oblong.
*Length of ovary.*—Medium.
*Color of ovary.*—Strong yellow green. (R.H.S. 144A, JHS 3507).
*Number of flowers.*—Few.
*Flower fragrance.*—Absent.
*Floriferousness.*—Medium.
*Grade of seed fertility.*—Low.
*Grade of floral abscission.*—Medium.
*Blooming time.*—Early.
*Flowering duration.*—Short; May to June and September to October.

Physiological and ecological characteristics:
*Grade of cold resistance.*—Medium.
*Grade of heat resistance.*—Medium.
*Grade of disease resistance.*—Strong.
*Grade of pest resistance.*—Medium.

"Fuchsia hybrida 1" was used for examination as a comparison are as follows.

Plant:
*Growth habit.*—Spreading.
*Plant height.*—Medium.
*Grade of business.*—Medium.

Stem:
*Thickness.*—2.4 mm.
*Color.*—Red.
*Pubescence.*—Normal.
*Branching.*—Medium.
*Length of internode.*—Medium.

Leaf:
*Phyllotaxis.*—Opposite.
*Shape.*—Ovate.
*Tip form of leaf.*—Acute.
*Base form of leaf.*—Orbicular.
*Shape of margin.*—Dentate serrate.
*Length.*—44.5 mm.
*Width.*—23.4 mm.
*Thickness.*—0.3 mm.
*Color of upper surface of new leaf.*—Dark olive green. (R.H.S. 139A, JHS 3707).
*Color of upper surface of mature leaf.*—Dark yellowish green. (R.H.S. 139A, JHS 4007).
*Color of under surface of mature leaf.*—Moderate yellow green (R.H.S. 146B, JHS 3514) with deep red (R.H.S. 60A, JHS 0108) dots.
*Variegation on upper surface.*—Absent.
*Color of leaf vein.*—Purplish red.
*Luster.*—Absent.
*Pubescence of upper surface.*—Few.
*Pubescence of under surface.*—Few.
*Length of petiole.*—17.0 mm.
*Width of petiole.*—1.5 mm.
*Color of petiole.*—Deep red. (R.H.S. 60A, JHS 0108).
*Pubescence of petiole.*—Medium.

Flower:
*Inflorescence types.*—Leaf axil—single.
*Facing direction.*—Downward to horizontal.
*Type.*—Single.

*Diameter.*—37.6 mm.
*Length.*—29.1 mm.
*Diameter of corolla.*—Medium.
*Shape of petal.*—Obovate.
*Length of petal.*—18.1 mm.
*Width of petal.*—17.9 mm.
*Thickness of petal.*—0.3 mm.
*Number of petals.*—Medium; 4.
*Color of petal at the beginning of blooming time.*—Pinkish white. (R.H.S. 49C, JHS 0101).
*Color of petal at blooming time.*—Pinkish white. (R.H.S. 49C, JHS 0101).
*Variegated pattern of petal.*—Present; vein pattern.
*Color of variegated pattern of petal.*—Vivid red. (R.H.S. 57A, JHS 0107).
*Shape of sepal.*—Oblong.
*Tip form of sepal.*—Acute.
*Calyx rolling.*—medium (half up).
*Intorsion of sepal.*—Medium.
*Curvature of sepal.*—Flat.
*Length of sepal.*—30.5 mm.
*Width of sepal.*—7.9 mm.
*Thickness of sepal.*—0.5 mm.
*Number of sepals.*—Medium; 4.
*Color of sepal.*—Deep pink. (R.H.S. 51A, JHS 0113).
*Variegated patter on sepal.*—Present; vein pattern.
*Color of variegated pattern of sepal.*—Deep pink. (R.H.S. 51A, JHS 0113).
*Shape of calyx tube.*—Long-tubular.
*Thickness of calyx tube.*—4.4 mm.
*Length of calyx tube.*—9.0 mm.
*Color of calyx tube.*—Deep pink. (R.H.S. 51A, JHS 0113).
*Variegated pattern on calyx tube.*—Present; vein pattern.
*Color of variegated pattern of calyx tube.*—Vivid red. (R.H.S. 57A, JHS 0107).
*Length of pistil.*—Long.
*Color of pistil.*—Strong purplish pink. (R.H.S. 55A, JHS 9705).
*Color of stigma.*—Strong purplish pink. (R.H.S. 55A, JHS 9705).
*Length of stamen.*—Medium.
*Color of stamen.*—Strong purplish pink. (R.H.S. 55A, JHS 9705).
*Number of stamens.*—Medium; 8.
*Thickness of peduncle.*—Medium.
*Length of peduncle.*—Medium..
*Color of peduncle.*—Vivid yellow green. (R.H.S. 140A, JHS 3105).
*Shape of ovary.*—Elliptic.
*Length of ovary.*—Short.
*Color of ovary.*—Strong yellow green (R.H.S. 143A, JHS 3711).
*Number of flowers.*—Medium.
*Flower fragrance.*—Absent.
*Floriferousness.*—Few.
*Grade of seed fertility.*—Medium.
*Grade of floral abscission.*—Easy.
*Blooming time.*—Early.
*Flowering duration.*—Short; May to June and September to October.

Physiological and ecological characteristics:
*Grade of cold resistance.*—Medium.
*Grade of heat resistance.*—Medium.
*Grade of disease resistance.*—Strong.
*Grade of pest resistance.*—Medium.

This new and distinct variety of fuchsia plant, "Sanihanf", was asexually reproduced by cutting at the aforementioned at the Plant Biotechnology Laboratory of SUNTORY Ltd. and the Plant Research Center of NISHINOMIYA-shi, and the homogeneity and stability thereof were confirmed.

SUMMARY OF THE VARIETY

The new variety of fuchsia plant has a nutant growth habit, low plant height, strong bushy and leaf axil - rosette inflorescence types is very different from a similar variety, "Fuchsia hybrida 2"(♀) having spreading growth habit and weakly bushy. The new variety of fuchsia plant has a great profusion blooms and very long flowering duration and deep violet to moderate purple flower petals without variegated pattern, which is clearly distinguished from "Fuchsia hybrida 2"(♀)" having deep purple flower petals with splashed pattern and vein pattern. The new variety of fuchsia plant has a high resistance to heat, cold and disease and it is able to growing in outdoor garden during the term of intensity of summer heat.

DESCRIPTION OF THE VARIETY

Figure 1:
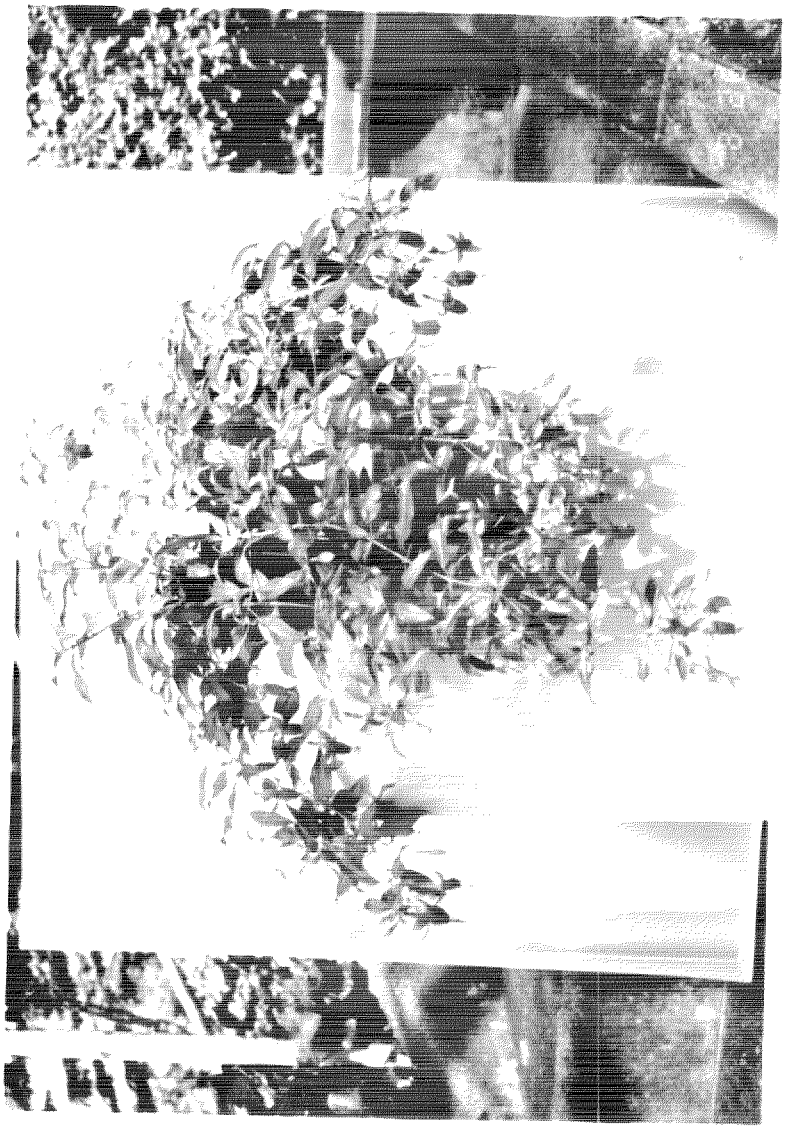
FIG. 1 is a photograph giving a partial view of the new variety of fuchsia plant planted in a flower pot.
Figure 2:
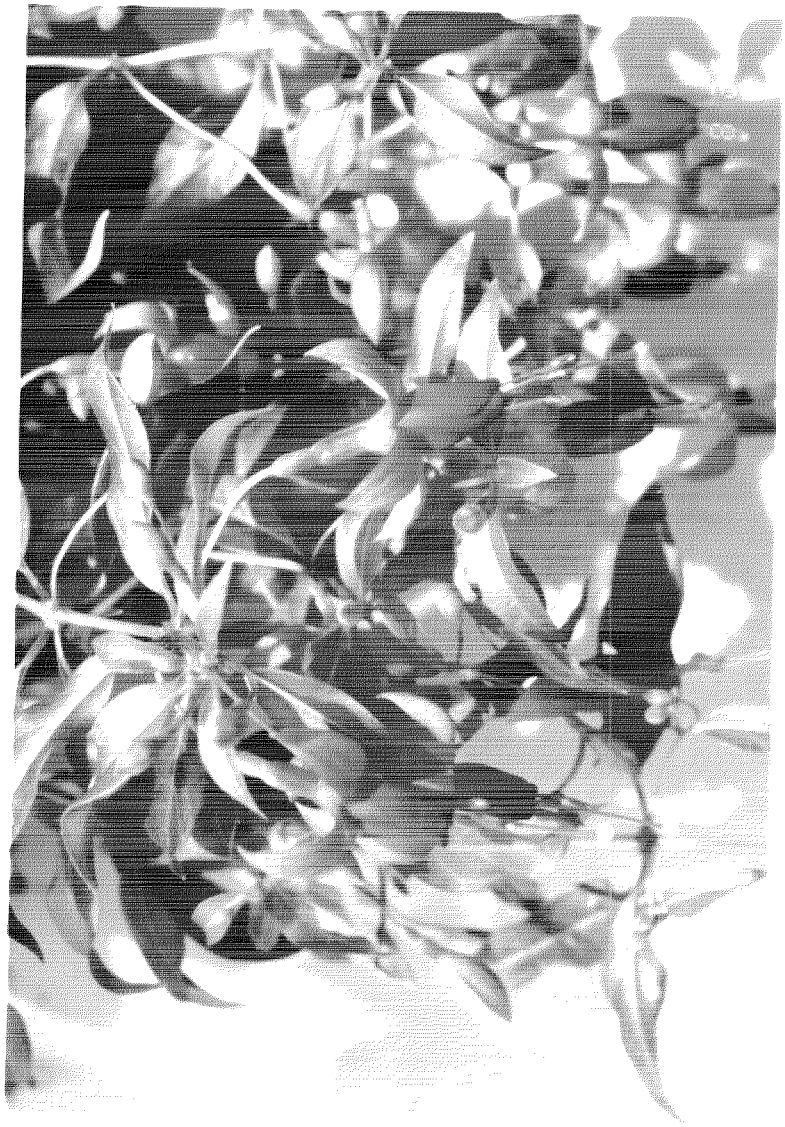
FIG. 2 is a photograph of flowers of the new variety of fuchsia plant.

The botanical characteristics of the new and distinct variety of fuchsia plant "Sanihanf" are as follows.

Plant:
*Growth habit.*—Nutant.
*Plant height.*—Low.
*Grade of bushiness.*—Many branches.

Stem:
*Thickness.*—2.7 mm.
*Color.*—Red.
*Pubescence.*—Few.
*Branching.*—Medium.
*Length of internode.*—Medium.

Leaf:
*Phyllotaxis.*—Opposite, partially 3-verticillate.
*Shape.*—Oblong.
*Tip form of leaf.*—Acute.
*Base form of leaf.*—Orbicular.
*Shape of margin.*—Dentate serrate.
*Length.*—43.8 mm.
*Width.*—20.8 mm.
*Thickness.*—0.6 mm.
*Color of upper surface of new leaf.*—Grayish olive green. (R.H.S. 137A, JHS 3716).
*Color of upper surface of mature leaf.*—Grayish olive green. (R.H.S. 137A, JHS 3716).
*Color of under surface of mature leaf.*—Moderate yellow green. (R.H.S. 146B, JHS 3514).
*Variegation on upper surface.*—Absent.
*Color of leaf vein.*—Pale green.
*Luster.*—Absent.
*Pubescence of upper surface.*—Absent.
*Pubescence of under surface.*—Absent.
*Length of petiole.*—9.1 mm.

*Width of petiole.*—1.3 mm.
*Color of petiole.*—Dark red. (R.H.S. 59A, JHS 0110).
*Pubescence of petiole.*—Few.

Flower:
*Inflorescence types.*—Leaf axil—rosette.
*Facing direction.*—Downward to horizontal.
*Type.*—Single.
*Diameter.*—49.1 mm.
*Length.*—32.4 mm.
*Diameter of corolla.*—Medium.
*Shape of petal.*—Obovate.
*Length of petal.*—15.6 mm.
*Width of petal.*—14.7 mm.
*Thickness of petal.*—0.3 mm.
*Number of petals.*—Medium; 4.
*Color of petal at the beginning of blooming time.*—Deep violet. (R.H.S. 93A, JHS 8006).
*Color of petal at blooming time*—Moderate purple. (R.H.S. 83A, JHS 8312).
*Variegated pattern of petal.*—Absent.
*Shape of sepal.*—Oblong.
*Tip form of sepal.*—Acute.
*Calyx rolling.*—Medium (half up).
*Intorsion of sepal.*—None.
*Curvature of sepal.*—Outcurve.
*Length of sepal.*—26.3 mm.
*Width of sepal.*—8.1 mm.
*Thickness of sepal.*—0.6 mm.
*Number of sepals.*—Medium; 4.
*Color of sepal.*—Vivid red. (R.H.S. 52A, JHS 0106).
*Variegated pattern on sepal.*—Absent.
*Shape of calyx tube.*—Long-tubular.
*Thickness of calyx tube.*—3.7 mm.
*Length of calyx tube.*—11.6 mm.
*Color of calyx tube.*—Vivid red. (R.H.S. 52A, JHS 0106).
*Variegated pattern on calyx tube.*—Absent.
*Length of pistil.*—Long.
*Color of pistil.*—Deep purplish pink. (R.H.S. 55A, JHS 9705).
*Color of stigma.*—Strong purplish pink. (R.H.S. 67D, JHS 8904).
*Length of stamen.*—Long.
*Color of stamen.*—Strong purplish red. (R.H.S. 60D, JHS 9708).

*Number of stamens.*—Medium; 8.
*Thickness of peduncle.*—Medium.
*Length of peduncle.*—Medium..
*Color of peduncle.*—Pale yellowish pink. (R.H.S. 37D, JHS 1002).
*Shape of ovary.*—Oblong.
*Length of ovary.*—Medium.
*Color of ovary.*—Strong yellow green. (R.H.S. 144A, JHS 3311).
*Number of flowers.*—Medium.
*Flower fragrance.*—Absent.
*Floriferousness.*—Many.
*Grade of seed fertility.*—Medium.
*Grade of floral abscission.*—Medium.
*Blooming time.*—Early.
*Flowering duration.*—Long; early May to the middle of December.

Physiological and ecological characteristics:
*Grade of cold resistance.*—Strong.
*Grade of heat resistance.*—Strong.
*Grade of pest resistance.*—Medium.

This new variety of fuchsia plant is most suitable for flower potting, particularly in hanging pots.

The plant of this new variety "Sanihanf" is presently planted and maintained at the Plant Biotechnology Laboratory of SUNTORY Ltd., residing at 863-1, Aza-Iketani, Oomori-cho, Youkaichi-shi, Shiga-ken, Japan and at the Plant Research Center of NISHINOMIYA-shi, residing at 1-1, Kitayama-cho, Nishinomiya-shi, Hyogo-ken, Japan.

We claim:

1. A new and distinct variety of fuchsia plant, substantially as herein illustrated and described, characterized particularly as to novelty by (A) being a nutant growth habit plant with low plant height and strong bushy, (B) great profusion blooms, the whole bush remaining in bloom for a considerable period of time, and very long flowering duration, (C) having flowers which are single without variegated pattern on petals which is deep violet to moderate purple color, (D) having vivid red sepals without variegated pattern and vivid red calyx tube without variegated pattern, and (E) a high resistance to heat, cold and disease.

* * * * *